(12) United States Patent
Rajala et al.

(10) Patent No.: US 8,622,984 B2
(45) Date of Patent: Jan. 7, 2014

(54) DISPOSABLE UNDERGARMENT AND RELATED MANUFACTURING EQUIPMENT AND PROCESSES

(75) Inventors: Gregory J. Rajala, Neenah, WI (US); Steven C. Gehling, Oshkosh, WI (US); Paul D. Suke, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/913,362

(22) Filed: Oct. 27, 2010
(Under 37 CFR 1.47)

(65) Prior Publication Data
US 2011/0040277 A1     Feb. 17, 2011

Related U.S. Application Data

(60) Continuation of application No. 11/240,262, filed on Sep. 30, 2005, now abandoned, which is a continuation-in-part of application No. 09/548,231, filed on Apr. 12, 2000, now abandoned, which is a continuation of application No. 08/937,225, filed on Sep. 11, 1997, now Pat. No. 6,049,916, which is a division of application No. 08/382,108, filed on Jan. 31, 1995, now Pat. No. 5,745,922.

(51) Int. Cl.
*A61F 13/15* (2006.01)
*A61F 13/20* (2006.01)

(52) U.S. Cl.
USPC ............................. 604/385.27; 604/385.25

(58) Field of Classification Search
USPC ............ 604/358, 367, 385.01, 385.24–385.3, 604/386, 396, 402
See application file for complete search history.

(56) References Cited

U.S. PATENT DOCUMENTS 2,627,858 A   2/1953   Miller
2,890,701 A   6/1959   Weinman
(Continued)

FOREIGN PATENT DOCUMENTS

CA   2105455 C   1/2005
EP   0048010 A1  3/1982
(Continued)

OTHER PUBLICATIONS

Kimberly-Clark Worldwide, Inc.'s Fifth Supplemental Response to Interrogatory Nos. 5 and 8 and Third Supplemental Response to Interrogatory No. 7.
(Continued)

*Primary Examiner* — Michele M Kidwell
(74) *Attorney, Agent, or Firm* — Dorty & Manning, P.A.

(57) ABSTRACT

This invention pertains to a three dimensional disposable panty, subassemblies of the panty, and an apparatus and methods for making the panty and subassemblies. The panty is designed to hold a primary absorbent sanitary pad. The panty may have elasticized leg and waist openings and be stretchable about the hip and stomach regions of a user. the panty provides backup protection to control egress of fluids that leak or seep around or through the primary sanitary pad. The panty includes a secondary absorbent positioned in the crotch area and extending into the body of the disposable panty, front and back, and preferably over the leg elastics to trap, inside the panty, leakage from the primary absorbent, and to prevent strike through onto e.g. outer clothing and bed linen. The apparatus and methods facilitate assembling leg elastics and crotch elastics into the panty subassemblies while assembling a series of panty subassemblies in a continuous web structure at a constant, or relatively constant, continuous and efficient speed.

16 Claims, 12 Drawing Sheets

(56) References Cited

U.S. PATENT DOCUMENTS

| | | |
|---|---|---|
| 3,488,778 A | 1/1970 | Goujon et al. |
| 3,560,292 A | 2/1971 | Butter |
| 3,599,640 A | 8/1971 | Larson |
| 3,654,929 A | 4/1972 | Nilsson et al. |
| 3,886,941 A | 6/1975 | Duane et al. |
| 3,981,306 A | 9/1976 | Krusko |
| 4,019,517 A | 4/1977 | Glassman |
| 4,022,210 A | 5/1977 | Glassman |
| 4,205,679 A | 6/1980 | Repke et al. |
| 4,244,367 A | 1/1981 | Rollenhagen |
| 4,309,236 A | 1/1982 | Teed |
| 4,360,398 A | 11/1982 | Sabee |
| 4,402,688 A | 9/1983 | Julemont |
| 4,405,397 A | 9/1983 | Teed |
| 4,425,130 A | 1/1984 | DesMarais |
| 4,430,086 A | 2/1984 | Repke |
| 4,464,217 A | 8/1984 | Dickover et al. |
| 4,479,836 A | 10/1984 | Dickover et al. |
| 4,585,447 A | 4/1986 | Karami |
| 4,610,680 A | 9/1986 | LaFleur |
| 4,619,649 A | 10/1986 | Roberts |
| 4,642,819 A | 2/1987 | Ales et al. |
| 4,699,621 A | 10/1987 | Stevens et al. |
| 4,743,241 A | 5/1988 | Igaue et al. |
| 4,801,345 A | 1/1989 | Dussaud et al. |
| 4,816,025 A | 3/1989 | Foreman |
| 4,820,296 A | 4/1989 | Masliyah |
| 4,854,989 A | 8/1989 | Singheimer |
| 4,892,528 A | 1/1990 | Suzuki et al. |
| 4,897,084 A | 1/1990 | Ternstrom et al. |
| 4,960,414 A | 10/1990 | Meyer |
| 5,055,103 A | 10/1991 | Nomura et al. |
| 5,069,678 A | 12/1991 | Yamamoto et al. |
| 5,080,741 A | 1/1992 | Nomura et al. |
| 5,092,861 A | 3/1992 | Nomura et al. |
| 5,147,487 A | 9/1992 | Nomura et al. |
| 5,163,932 A | 11/1992 | Nomura et al. |
| 5,171,239 A | 12/1992 | Igaue et al. |
| 5,188,627 A | 2/1993 | Igaue et al. |
| 5,197,960 A | 3/1993 | Nomura et al. |
| 5,389,173 A | 2/1995 | Merkatoris et al. |
| 5,449,353 A | 9/1995 | Watanabe et al. |
| 5,500,075 A | 3/1996 | Herrmann |
| 5,509,914 A | 4/1996 | Osborn |
| 5,525,175 A | 6/1996 | Blenke et al. |
| 5,545,275 A | 8/1996 | Herrin et al. |
| H1614 H | 11/1996 | Mayer et al. |
| 2,581,904 A | 11/1996 | Burns |
| 5,622,581 A | 4/1997 | Ducker et al. |
| 5,634,917 A | 6/1997 | Fujioka et al. |
| 5,745,922 A | 5/1998 | Rajala et al. |
| 5,788,797 A | 8/1998 | Herrin et al. |
| 5,817,087 A | 10/1998 | Takabayashi et al. |
| 5,836,931 A | 11/1998 | Toyoda et al. |
| 5,873,869 A | 2/1999 | Hammons et al. |
| 5,940,887 A | 8/1999 | Rajala et al. |
| 6,013,065 A | 1/2000 | Suzuki et al. |
| 6,049,916 A | 4/2000 | Rajala et al. |
| 6,098,203 A | 8/2000 | Rajala et al. |
| 6,132,410 A | 10/2000 | Gompel et al. |
| 6,179,820 B1 | 1/2001 | Fernfors |
| 6,217,690 B1 | 4/2001 | Rajala et al. |
| 6,240,569 B1 | 6/2001 | Van Gompel et al. |
| 6,260,211 B1 | 7/2001 | Rajala et al. |
| 6,367,089 B2 | 4/2002 | Van Gompel et al. |
| 6,375,646 B1 | 4/2002 | Widlund et al. |
| 6,391,013 B1 | 5/2002 | Suzuki et al. |
| 6,417,425 B1 | 7/2002 | Whitmore et al. |
| 6,702,798 B2 | 3/2004 | Christoffel et al. |
| 7,000,260 B2 | 2/2006 | Rajala et al. |
| 8,142,590 B2 | 3/2012 | Rajala et al. |
| 8,257,331 B2 | 9/2012 | Fujioka et al. |
| 2002/0152540 A1 | 10/2002 | Van Gompel et al. |
| 2005/0065494 A1 | 3/2005 | Harriott |
| 2006/0064069 A1 | 3/2006 | Rajala et al. |
| 2008/0287897 A1 | 11/2008 | Reyes et al. |
| 2008/0300568 A1 | 12/2008 | Fujioka et al. |
| 2011/0040277 A1 | 2/2011 | Rajala et al. |

FOREIGN PATENT DOCUMENTS

| | | |
|---|---|---|
| EP | 0048011 A1 | 3/1982 |
| EP | 0073183 A1 | 3/1983 |
| EP | 0405575 A1 | 1/1991 |
| EP | 0475419 A1 | 3/1992 |
| EP | 0487921 A2 | 6/1992 |
| EP | 0 626 161 a1 * | 11/1994 |
| EP | 0623331 A2 | 11/1994 |
| EP | 0626161 A1 | 11/1994 |
| EP | 0692233 A1 | 1/1996 |
| EP | 1325723 A2 | 7/2003 |
| EP | 1327430 A2 | 7/2003 |
| FR | 2177425 A1 | 11/1973 |
| FR | 2517524 A1 | 6/1983 |
| GB | 2112268 A | 7/1983 |
| GB | 2189133 A | 10/1987 |
| GB | 2244422 A | 12/1991 |
| GB | 2253131 A | 9/1992 |
| JP | 3139349 A | 6/1991 |
| JP | 3176053 A | 7/1991 |
| JP | 4028363 A | 1/1992 |
| JP | 4028364 A | 1/1992 |
| JP | 4161152 A | 6/1992 |
| JP | 4289201 A | 10/1992 |
| JP | 7136210 A | 5/1995 |
| JP | 8024290 A | 1/1996 |
| JP | 8024291 A | 1/1996 |
| WO | WO 9009159 A1 | 8/1990 |
| WO | 96/23477 | 8/1996 |
| WO | WO 9843584 A1 | 10/1998 |

OTHER PUBLICATIONS

Defendants' Third Supplemental Responses to Plaintiff's First Set of Interrogatories (Nos. 3 and 4).
Defendants' Revised Third Supplemental Responses to Plaintiff's First Set of Interrogatories (Nos. 3 and 4).
Kimberly-Clark Worldwide, Inc.'s Memorandum in Support of Its Proposed Claim Constructions.
Plaintiff's Response to Defendants' Third Set of Interrogatories (No. 9).
Plaintiff's Responses to Defendants' Second Set of Interrogatories (Nos. 7-8).
Kimberly-Clark Worldwide, Inc.'s First Supplemental Response to First Quality's Interrogatory No. 8.
Kimberly-Clark Worldwide, Inc.'s First Supplemental Response to Interrogatory No. 7 and Second Supplemental Response to Interrogatory No. 8 (Redacted).
December 7, 2010 Order Granting Kimberly-Clark Worldwide, Inc.'s Motion for Clarification.
First Quality's Responsive Claim Construction Brief.
Kimberly-Clark Worldwide, Inc.'s Reply Memorandum in Support of Its Proposed Claim Constructions (Redacted).
Transcript of June 9, 2010 Markman Hearing.
September 30, 2010 Claim Construction Ruling.
Plaintiff's Motion for Clarification of the Claim Construction for the Rajala '922, '203, '211, and '260 Patents.
Plaintiff's Brief in Support of Its Motion for Clarification of the Claim Construction for the Rajala '922, '203, '211, and '260 Patents.
First Quality's Opposition to Plaintiff's Motion for Clarification of the Claim Construction for the Rajala '922, '203, '211, and '260 Patents.
Plaintiff's Reply Brief in Support of Its Motion for Clarification of the Claim Construction for the Rajala '922, '203, '211, and '260 Patents.
Kimberly-Clark Worldwide, Inc.'s Fifth Supplemental Response to Interrogatory No. 7.
K-C's Third Supplemental Response to Interrogatory No. 1 and Sixth Supplemental Response to Interrogatory No. 8 (Redacted).

(56) References Cited

OTHER PUBLICATIONS

Kimberly-Clark Worldwide, Inc.'s Eighth Supplemental Response to Interrogatory No. 8 (Part I—Redacted).
Kimberly-Clark Worldwide, Inc.'s Eighth Supplemental Response to Interrogatory No. 8 (Part III—Redacted).
Kimberly-Clark Worldwide, Inc.'s Third Supplemental Response to Interrogatory No. 12 (Redacted).
K-C's Fourth Supplemental Response to Interrogatory No. 12 and Second Supplemental Response to Interrogatory No. 19 (Redacted).
K-C's Seventh Supplemental Response to Interrogatory No. 12 (Redacted).
K-C's Eight Supplemental Response to First Qualitys Interrogatory No. 8 (Part ll—Redacted).
Defendants' Motion for Summary Judgment of Noninfringement.
Defendants' Brief in Support of Their Motion for Summary Judgment of Non-Infringement.
Defendants' Statement of Material Facts in Support of Their Motion for Summary Judgment of Noninfringement.
Declaration of Tony Silwanowicz in Support of Defendants' Motion for Summary Judgment of Noninfringement.
K-C's Motion for Partial Summary Judgment of Infringement.
K-C's Brief in Support of Its Cross-Motion for Partial Summary Judgment of Infringement and in Opposition to First Quality's Motion for Summary Judgment of Noninfringement (Redacted).
K-C's Combined Repsonse to First Quality's Local Rule 56.1 Statement of Material Facts (Redacted).
Bridget Balogh's Declaration in Support of (i) K-C's Motion for Partial Summary Judgment of Infringement and (ii) K-C's Opposition to First Quality's Motion for Summary Judgment of Non-Infringement.
First Quality's Opposition to K-C's Cross-Motion for Summary Judgment and Reply Brief in Support of Summary Judgment (Redacted).
First Quality's Response to K-C's Local Rule 56.1 Statement.
Plaintiff's Combined Reply in Support of Its Cross-Motion for Partial Summary Judgment of Infringement and Sur-Reply in Opposition to First Quality's Motion for Summary Judgment (Redacted).
Order Denying FQ's Motion for Partial Summary Judgment and 414 and KC's Cross Motion for Partial Summary Judgment filed by KC, Jan. 31, 2012.
European Search Report, EP03006646, dated Mar. 18, 2004.
European Search Report, EP03006647, dated Mar. 18, 2004.
European Search Report, EP03006648, dated Mar. 18, 2004.
English language abstract for JP 4161152, published Jun. 4, 1992.
English language abstract for JP 4289201, published Oct. 14, 1992.
English language abstract for JP 7136210, published May 30, 1995.
English language abstract for JP 3139349, published Jun. 13, 1991.
English language abstract for EP 0 475 419, published Mar. 18, 1992.
English language abstract for EP 0 048 011, published Mar. 24, 1982.
English language abstract for JP 3176053, published Jul. 31, 1991.
English language abstract for EP 0 405 575, published Jan. 2, 1991.
English language abstract for JP 8024291, published Jan. 30, 1996.
English language abstract for JP 8024290, published Jan. 30, 1996.
Search Report for PCT/US2006/034806 dated Feb. 28, 2007.
Rajala et al, 95/002,369, Dec. 7, 2012.
Rajala et al, 95/002,362, Dec. 7, 2012.
Written Opinion of the ISA for PCT/US2006/034806, dated Apr. 1, 2008.
Rajala et al, 90/012,813, Mar. 22, 2013—Request and Order Granting Request.
Rajala et al, 90/012,814, Mar. 22, 2013—Request and Order Granting Request.
Kimberly-Clark's Ninth Supplemental Response to Interrogatory No. 7.
Kimberly-Clark's Twelfth Supplemental Response to Interrogatory No. 8 (Redacted).
First Quality's Eighth Supplemental Response to Kimberly-Clark's First Set of Interrogatories (No. 3) (Redacted).
Expert Report and Declaration of Bridget Balogh on the Infringement of US Pat. Nos. 5,745,922; 6,098,203; 6,260,211; 7,000,260; and 5,940,887 (Redacted).
Rebuttal Expert Report and Declaration of Bridget Balogh Relating to US Pat. Nos. 5,745,922; 6,098,203; 6,260,211; and 7,000,260 (Redacted).
Expert Report of Daniel D. Gardner Regarding the Invalidity of US Pat. Nos. 5,745,922; 6,098,203; 6,260,211; and 7,000,260 to Rajala et al.
Rebuttal EXpert Report of Daniel D. Gardner Regarding the Non-Infringement of US Pat. Nos. 5,745,922; 6,098,203; 6,260,211; and 7,000,260 (Redacted).
Supplemental Expert Report of Daniel D. Gardner Regarding the invalidity of US Pat. Nos. 5,745,922; 6,098,203; 6,260,211; and 7,000,260 to Rajala et al.
Kimberly-Clark's Expedited Motion and Request for Expedited Briefing and Ruling to Strike and Preclude First Quality's New and Untimely Invalidity, Expert Report and Opinions.
Kimberly-Clark's Memorandum in Support of its Expedited Motion and Request for Expedited Briefing and Ruling to Strike and Preclude.
First Quality's Cross-Motion in the AlternatiVe to Strike Kimberly-Clark's Supplemental Expert Report and Opinions and Preclude Kimberly-Clark's Use of Previously Unidentified Witnesses, Evidence, and Contentions.
First Quality's Memorandum in Opposition to Kimbehy-Clark's Motion to Strike and Preclude First Quality's Expert Report; and (2) in Support of First Quality's Cross-Motion.
Kimberly-Clark's Reply in Support of its Expedited Motion to Strike and Preclude First Quality's New and Untimely Invalidity Defense, Expert Report, and Opinions.
Kimberly-Clark's Opposition to First Quality's Cross-Motion in the Alternative to Strike Kimberly-Clark's Supplemental Expert Report and Opinions and Preclude.
Kimberly-Clark's Motion for Summary Judgment that the Suzuki Reference is not Prior Art to and Therefore Cannot Invalidate the '922, '203, '211, and '260 Rajala Patents.
Gregory Rajala's Declaration in Support of Kimberly-Clark's Motion for Summary Judgment that the Suzuki Reference is not Prior Art to the Rajala Patents (Redacted).
Kimberly-Clark's Statement of Material Facts in Support of Its Motion for Summary Judgment that Suzuki is not Prior Art.
Kimberly-Clark's Memorandum in Support of its Motion for Summary Judgment that Suzuki is Not Prior Art and Therefore Cannot Invalidate the '922, '203, '211 and '260 Rajala Patents.
First Quality's Reply Memorandum in Support of its Cross-Motion in the Alternative to Strike Kimberly-Clark's Supplemental Expert Report and Opinions and Preclude.
Kimberly-Clark's Motion for Leave to File a Sur-Reply in Opposition to First Quality's Cross-Motion in the Alternative to Strike Kimberly-Clark's Supplemental Expert Report and Opinions.
First Quality's Motion for Leave to File a Sur-Reply to Kimberly-Clark's Sur-Reply in Opposition to First Quality's Cross-Motion in the Alternative to Strike Kimberly-Clark's Supplemental Expert Report and Opinions.
Order Granting Kimberly-Clark's Motion to Strike [621] and Deny First Quality's Cross Motion to Strike.
First Quality's Response to Kimberly-Clark's Statement of Undisputed Material Facts in Support of Its Motion re '922 Rajala Patents (Redacted).
First Quality's Memo in Opposition to Kimberly-Clark's MSJ re '922 Rajala Patents (Redacted).
Daniel D. Gardner's Declaration in Support of First Quality's Opposition to Kimberly-Clark's Motion for Summary Judgment that the Suzuki is not Prior Art.
Kimberly-Clark's Reply in Support of its Motion for Summary Judgment that the Suzuki Reference is not Prior Art to the Rajala Patents.
Kimberly-Clark's Response to First Quality's Counterstatement of Material Fact No. 13.
Letter from Ira E. Silfin to the Court re Rajala Patents.
First Quality's Motion for Leave to File a Sur-Reply to Kimberly-Clark's Reply in Support of its Motion for Summary Judgment that the Suzuki Reference is not Prior Art to Rajala Patents.

(56) References Cited

OTHER PUBLICATIONS

Kimberly-Clark's Letter to the Court re Rajala Briefing and Accompanying Exhibits.
Letter to the Court re First Quality's Response to Kimberly-Clark's Letter of Dec. 28, 2012 (ECF No. 712) Regarding the Rajala Patent.
Letter from Kimberly-Clark to the Court Responding to First Quality's Jan. 2, 2013 Letter.
Kimberly-Clark's Opposition to First Quality's Motion for Leave to File a Sur-Reply to Kimberly-Clark's Reply in Support of its Motion that the Suzuki is not Prior Art to the '922 Rajala Patent.
Order re First Quality's Letter Request for a Stay is Denied.
First Quality's Renewed Motion for Summary Judgment that the Accused Products do not infringe US Pat, Nos. 5,745,922; 6,098,203; 6,260,211; and 7,000,260 to Rajala.
Brief in Support of their Renewed Motion for Summary Judgment that the Accused Products do not Infringe Rajala.
First Quality's Statement of Material Facts in Support of their Renewed Motion for Summary Judgment of Non-Infringement.
Kimberly-Clark's Opposition to First Quality's Renewed Motion for Summary Judgment of Non-Infringement of Kimberly-Clark's US Pat, Nos. 5,745,922; 6,098,203; 6,260,211; and 7,000,260.
Kimberly-Clark's Combined Response to First Quality's Statement of Material Facts and Kimberly Clark's Statement of Material Facts Regarding First Quality's Renewed Motion of Non-Infringement.
First Quality's Reply Bilef in Support of its Renewed Motion for Summary Judgment of Non-Infringement of Kimberly-Clark's Rajala Patents.
First Quality's Response to Kimberly-Clark's Additional Statement of Material Facts in Response to First Quality's Local Rule 56.1 Statement of Material Facts.
Kimberly-Clark's Sur-Reply in Opposition to First Quality's Renewed Motion for Summary Judgment of Non-Infringement of Kimberly-Clark's US Pat, Nos. 5,745,922; 6,098,203; 6,260,211; and 7,000,260.
First Quality's Sur-Sur Reply Brief in Support of Its Renewed Motion for Summary Judgment of Non-Infringement of Kimberly-Clark's Rajala Patents.
Kimberly-Clark's Response to First Quality's Sur-Sur-Reply Concerning First Quality's Renewed Motion for Summary Judgment of Non-Infringement of Kimberly-Clark's US Pat, Nos. 5,745,922; 6,098,203; 6,260,211 and 7,000,260.
First Quality's Brief in Support of its Renewed Motion for Summary Judgment of Non-Infringement of the Rajala Patents.
Rajala et al, U.S. Appl. No. 08/453,536, filed May 30, 1995, Abandoned.
Rajala et al, U.S. Appl. No. 08/924,943, filed Sep. 8, 1977, Abandoned.
Rajala et al, U.S. Appl. No. 08/548,231, filed Apr. 12, 2000, Abandoned.
Rajala et al., 95/002,362, filed Sep. 14, 1995.
Rajala et al, 95/002,369, filed Sep. 14, 1995.

\* cited by examiner

DISPOSABLE UNDERGARMENT AND RELATED MANUFACTURING EQUIPMENT AND PROCESSES

RELATED APPLICATIONS

The present application is a continuation application of and claims priority to co-pending U.S. patent application Ser. No. 11/240,262, filed Sep. 30, 2005, which is a continuation-in-part application of U.S. patent application Ser. No. 09/548,231, filed Apr. 12, 2000, now abandoned, which is a continuation of prior U.S. patent application Ser. No. 08/937,225, filed Sep. 11, 1997, now U.S. Pat. No. 6,049,916, which is a divisional of prior U.S. patent application Ser. No. 08/382,108 filed on Jan. 31, 1995, now U.S. Pat. No. 5,745,922, each of which are incorporated herein by reference in their entirety.

BACKGROUND OF THE INVENTION

Undergarments are made typically of cotton and/or synthetic materials. The cotton and synthetic panties typically do not offer barrier protection. Often the synthetic undergarments have a cotton lined crotch to absorb vaginal discharges or perspiration. The absorbent/barrier properties of regular undergarments are minimal such that any vaginal discharge and/or heavy perspiration may strike through onto outer clothing; i.e., liquid penetrates from the interior to the exterior of the panty.

Panty liners and feminine care sanitary napkins or pads used with regular undergarments have polyethylene backings that provide some barrier properties inhibiting liquid strike through. However, if the vaginal discharge extends to the sides or the ends of the pads, the discharge can leak or seep around an edge of the pad and onto the undergarment. Such leakage can stain the undergarment. Depending upon the amount of leakage, liquid may strike through or go around the undergarment and stain outer clothing and/or bedding. Women with heavy liquid flows may often use one or more maxi pads, double pads and/or tampons alone, or in combination, and change these pads and tampons frequently to prevent embarrassing, messy leakage around the edges of the pads and/or staining of outer clothing. In some cases, during their heaviest flow days, some women will restrict their activities and stay home.

Many women experience some leakage of menses from their pads to their undergarments. This varies from being limited to a small number of pads leaking onto only the undergarment during light flow to more prevalent leakage onto the wearer's outer clothing on pads worn during heavy flow. Normally this leakage occurs at the side of the pad, although end leakage is also a problem. Placement of maxi pads and overnight pads in the crotch of regular undergarments shows that, at best, the pads lay on the leg elastic and, at worst, overhang the leg elastics. This causes side leakage onto the undergarment and possibly onto outer clothing. Typical leakage from the pads is caused by poor fit of the pad to the body, improper positioning of the pad by the user and lack of absorbency. Leakage from the undergarment onto the outer clothing is typically due to incompatibility between the pad width and the panty crotch width and/or lack of barrier properties in the panty material around the edge portion of the pad.

BRIEF SUMMARY OF THE INVENTION

The present invention broadly includes a three dimensional, disposable, discrete panty, subassemblies of the panty, and apparatus and methods for making the panty.

In one aspect of the invention, a method for attaching elastic to a crotch area of an undergarment includes the steps of cutting an elastic thread into a plurality of elastic sections; providing a secondary absorbent for receipt of at least one of the elastic sections, the secondary absorbent defining an inner side and an opposing outer side; attaching the elastic sections to the inner side of the secondary absorbent as the elastic sections and the secondary absorbent move in a machine direction; maneuvering the secondary absorbent with the elastic sections attached thereto to a non-machine direction; and attaching the secondary absorbent to a garment web moving in the machine direction, the elastic sections of the inner side disposed against an inner crotch portion of the garment web, the opposing outer side visible in the crotch portion. In this aspect, each elastic section is from about one inch to about three inches in length. Also in this aspect, the elastic sections are attached to the inner side of the secondary absorbent by an adhesive.

According to a further aspect of the invention, a disposable garment assembly includes a disposable garment defining a length and a width and including an outer cover having a front body portion and a back body portion, the front body portion and the back body portion being connected by a crotch portion, the outer cover, when laid out flat, having a length and a width, the front body portion and the back body portion being connected together to form a waist opening, a first leg opening and a second leg opening, the first and second leg openings having respective first and second front and back leg edge portions and corresponding first and second side leg edge portions connecting the front and back leg edge portions, the outer cover comprising a first layer, and a second layer having a front portion and a back portion, the second layer front portion disposed adjacent the front body portion of the outer cover, the second layer back portion disposed adjacent the back body portion of the outer cover; a first absorbent defining a length and a width, each respectively less than the length and the width of the disposable garment, the first absorbent further including a liquid impermeable outer sheet and a liquid permeable inner sheet, the liquid impermeable outer sheet having a front portion and a back portion, and a center portion therebetween, each of the liquid impermeable outer sheet front and back portions of the first absorbent disposed adjacent one of the respective second layer front and back body portions of the outer cover, the first absorbent having a first absorbent capacity; a second absorbent including a first side and a second side and having a second absorbent capacity, the second absorbent attached in the crotch portion and covering the width of the first absorbent, the second absorbent underlying the first absorbent on the liquid impermeable outer sheet of the first absorbent, the first side of the second absorbent disposed facing the liquid impermeable outer sheet, the first absorbent capacity of the first absorbent being greater than the second absorbent capacity of the second absorbent; and a plurality of crotch elastics extendably affixed between the outer cover and the second side of the second absorbent proximate the crotch portion, the second absorbent affixed to the outer cover.

In this aspect of the invention, the second absorbent capacity of the second absorbent is about one-half the absorbent capacity of the first absorbent. For instance, the second absorbent capacity of the second absorbent can be about 3 grams to about 6 grams, more particularly, about 4 grams to about 6 grams. Also in this aspect of the invention, the second absorbent is a stain shield.

In a further aspect of the invention, a disposable garment has a length and a width, and includes an outer cover having front and back body portions connected by a crotch portion, the outer cover, when laid out flat, having a length between first and second ends and a width between first and second sides, the front and back body portions being connected together to form a waist opening and first and second leg opening. The outer cover in this aspect includes a first layer; a second layer having front and back body portions overlying respective front and back body portions of the outer cover; and a stain shield incorporated into the disposable garment, the stain shield having a length and a width and a garment facing side, the garment facing side having a front portion, a back portion and a center portion therebetween, the garment facing side of the center portion having a plurality of extensible crotch elastic pieces attached thereto proximate the crotch portion, the extensible crotch elastic pieces being disposed between the garment facing side and the outer cover of the crotch portion, the stain shield affixed to the outer cover, each of the garment facing side front and back portions of the stain shield disposed adjacent one of the respective second layer front and back portions, at least a portion of the stain shield having an overall total absorbent capacity of about 3 grams to about 6 grams. Also in this aspect, at least a portion of the absorbent has an overall total absorbent capacity of about 4 grams to about 6 grams.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The following detailed description is made in the context of an article including a disposable panty, and corresponding panty subassemblies, for holding a sanitary pad in place as a primary absorbent during use of the panty. It is readily apparent, however, that the present invention can be employed with other disposable sanitary articles, such as feminine tampons, incontinent garments and the like.

Figure 1:
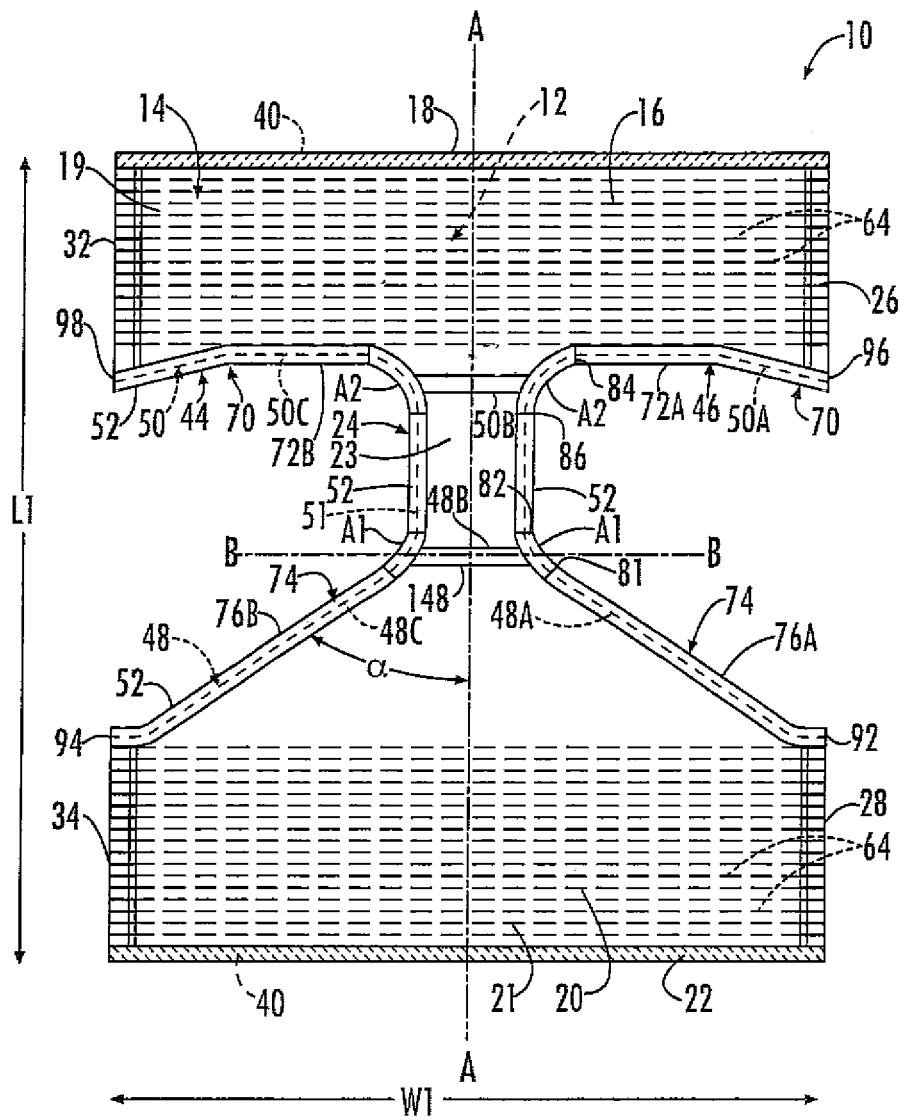
FIG. 1 is a plan view of a garment subassembly according to an aspect of the invention.
Figure 2:
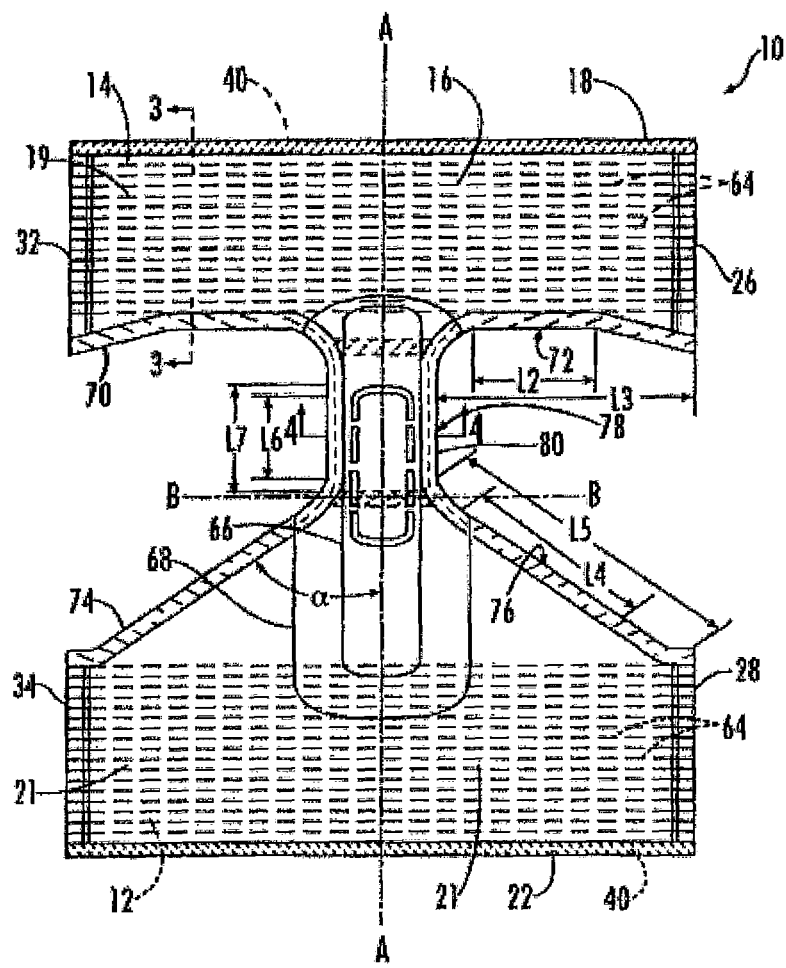
FIG. 2 is a plan view of the garment subassembly of FIG. 1, including a secondary absorbent in the crotch.
Figure 5:
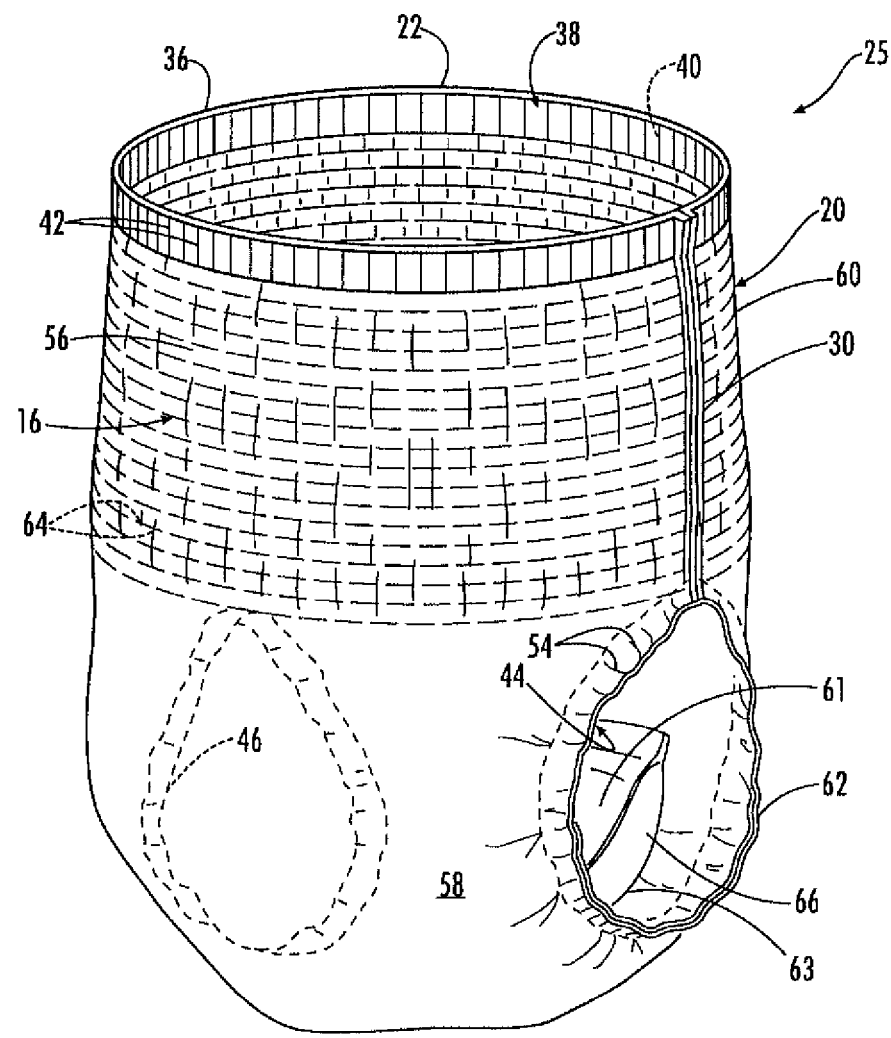
FIG. 5 is a perspective view of a disposable panty according to another aspect of the invention.

The panty subassembly 10 of FIG. 1 illustrates an embodiment of a two-layer panty subassembly prior to incorporation of the secondary absorbent. The panty subassembly of FIG. 2 illustrates the finished panty including all elements, but before the final steps of assembling the composite to form the panty structure. FIG. 5 shows the finally-assembled disposable panty structure.

Figure 3:
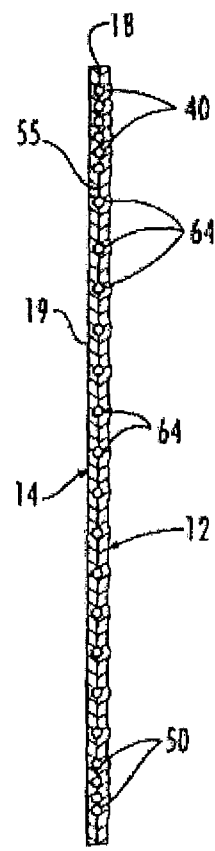
FIG. 3 is a cross section of the garment subassembly taken along line 3-3 of FIG. 2.

Referring to FIGS. 1-3, the panty subassembly 10 has an outer cover layer 12 generally defining the overall length "L1" and width "W1" of the subassembly, and a body side layer 14 secured to the outer cover layer. The panty subassembly 10 generally includes a front body portion 16 terminating at a front waist portion 18 as a first edge of the subassembly, a back body portion 20 terminating at a back waist portion 22 as a second edge of the subassembly, and a crotch portion 24.

The body side layer 14 includes a front layer element 19 generally overlying and secured to the outer cover layer 12 on the front body portion 16, and a back layer element 21 generally overlying and secured to the outer cover layer 12 on the back body portion 20. A space 23 separates the front layer element 19 from the back layer element 21.

Referring to FIGS. 2 and 5, for assembling the subassembly of FIG. 2 to form a panty 25 as in FIG. 5, a first side edge 26 of front body portion 16 is assembled with a first side edge 28 of the back body portion 20 to form a first side seal 30. Similarly, a second side edge 32 of the front body portion 16 is assembled with a second side edge 34 of the back body portion 20 to form a second side seal 36. The waist portions 18, 22 when assembled form a waist opening 38 for putting on and taking off the panty 25. The waist opening 38 is surrounded at least in part by a waist elastic 40. The waist elastic 40 is stretched and attached to the waist portions 18, 22 in the stretched state. The waist elastic 40 is released after attachment to produce waist folds or pleats 42 to allow expansion of the waist opening 38 so that the panty 25 can fit various sizes of people. Because users of this invention generally prefer a brief style panty, the front waist portion 18 preferably comes as high as the navel and is level around the wearer's waist. Having the panty at this height provides a snug fit. Alternative panty styles include bikini (e.g. regular leg cut or french leg cut) and hipster (e.g. regular leg cut or french leg cut).

Referring to FIGS. 1 and 5, the front body portion 16, the back body portion 20, and the crotch portion 24, in combination, form left and right leg openings 44 and 46, respectively, which are generally circular or oval in shape in the finally assembled panty 25. The leg openings 44 and 46 are formed by cutting away portions of the outer cover layer 12, and corresponding portions if any of body side layer 14. Each leg opening 44, 46 is surrounded at least in part by a back leg elastic 48, a front leg elastic 50, and a crotch elastic 51 between the back leg elastic and the front leg elastic. Each of the respective elastics 48, 50, 51 is adjacent the respective one of the edges 52 of the corresponding leg openings. The front and back leg elastics 48, 50 are secured between the outer cover layer 12 and the body side layer 14 by adhesive 55. The crotch elastics 51 are secured between outer cover layer 12 and a crotch elastic support sheet 53, also by adhesive 55. The elastics 48, 50, 51 are in the stretched state when secured to the outer cover layer 12. Accordingly, when the elastics, the outer cover layer, the body side layer, and the support sheet 53, are released after the elastics are secured to the outer cover layer, the elastics produce leg folds or pleats 54 at the edges of the leg openings 44, 46 to allow expansion of the leg openings 44, 46 to fit various sizes of legs.

The front body portion 16 may be divided into a front upper portion 56 and a front lower portion 58. Similarly, the back body portion 20 may be divided into a back upper portion 60 and a back lower portion 62. The upper portions 56 and 60 are preferably designed to include body elastics 64 which readily stretch to allow the wearer to put on the panty 25 and then readily contract to resume the normal release state of the body elastics. This ensures a close or snug fit to different body sizes and forms. A number of body elastics 64 are positioned on both the front and the back portions 56, 60, respectively, at positions between the waist opening 38 and the leg openings 44, 46, so that the panty 25 has a good fit, particularly around the body.

The lower body portions 58, 62 generally do not require the spaced elastics as in the upper body portions 56, 60, although the elastic threads may be used.

The width of the crotch portion 24 between the left and right crotch elastics 51 should be wide enough to accommodate laying the primary absorbent 66 between the edges 52 without having the primary absorbent 66 obstruct the crotch elastics 51. This allows the crotch elastics 51 to contract and draw up the sides of the crotch about the primary absorbent, to thus accommodate the thickness of the primary absorbent 66, and to give surface area within the crotch portion 24 of the panty, adjacent edges 52, to contain leakage from the primary absorbent 66.

The width of the crotch portion 24 between the elastics 51 should not be so wide as to seem bulky or uncomfortable. A suitable width is at least about 2.75 inches (70 mm) between the crotch elastics. Width of crotch portion 24 is advantageous from about 3 inches (76 mm) to about 3.5 inches (89 mm). Preferably, the width is about 3 inches (76 mm).

Preferably, the crotch elastics 51 are from about 0.375 inch (10 mm) to about 0.625 inch (16 mm) wide. More preferably, the width is about 0.5 inch (13 mm). Preferably, ruffle material on the edge of the leg openings 44, 46 outside the leg and crotch elastics 48, 50, 51 is less than about 0.25 (6 mm). More preferably, the ruffle material is less than about 0.125 inch (3 mm). It is most desirable to eliminate any ruffle material from the edges of the leg openings 44, 46.

The overall width of the crotch portion 24 includes the width between the left and right crotch elastics 51, the width of the crotch elastics, and any ruffle material outside the crotch elastics to the edges 52 of the leg openings. Preferably, the overall width of the crotch portion 24 should be at least about 4 inches (102 mm).

FIG. 2 shows the panty subassembly 10 of FIG. 1 with a secondary absorbent 68 secured in the crotch portion 24, over the outer cover layer 12 and parts of the front and back layer elements 19, 21 of the body side layer 14. The width of the secondary absorbent 68 is sized in relation to the width of the crotch portion 24. Preferably, the width of the secondary absorbent 68 is at least the width of the crotch portion 24 between the crotch elastics 51. More preferably, the width of the secondary absorbent is equivalent to the overall width of the crotch portion 24.

The secondary absorbent 68 should have sufficient capacity to absorb any flow or seepage of body fluid around or through the primary absorbent 66. The secondary absorbent 68 should preferably have a capacity and thickness substantially less than that of the primary absorbent 66, thus providing a nonbulky and flexible fit. The secondary absorbent 68 should have a total capacity of about one-half the capacity of the primary absorbent 66. Preferably, the secondary absorbent 68 should have a total capacity of at least about 3 grams and not more than 6 grams. More preferably, the total capacity of the secondary absorbent 68 should be from about 4 grams to about 6 grams. However, the basis weight of, or the type of, the secondary absorbent 68 should be selected to provide resistance to flexibility of less than around 400 grams, as measured by INDA Standard Test method IST 90.3-92 Standard Test Method for Handle-O-Meter Stiffness of Nonwoven Fabrics.

The secondary absorbent has a low stiffness. The low stiffness allows the absorbent and its barrier to remain attached to the conformable outer cover layer 12 and the body side layer 14 which conform to a wide range of body sizes and shapes. Preferably, the secondary absorbent has a stiffness of less than 400 grams along any axis tested, more preferably less than 300 grams along any axis and less than 100 grams along the axis parallel to the waist opening. The secondary absorbent alone will have a stiffness of less than 250 grams and preferably less than 100 grams along any axis and more preferably less than 75 grams along the axis parallel to the waist opening.

The overall length of the secondary absorbent 68 should be adequate to extend beyond the ends of the primary absorbent 66, in order to be properly positioned to receive liquid which flows or seeps around the edges of the primary absorbent 66. This overall length is typically at least about 15 inches (382 mm) thus extending beyond the crotch portion 24 along the longitudinal centerline A-A of the subassembly 10. The length should be in the range of about 15 inches (382 mm) to about 19 inches (484 mm). Preferably, the length of the secondary absorbent 68 is about 17 inches (433 mm).

The width of the secondary absorbent 68 beyond the crotch portion 24 should be at least as wide as the width of the crotch portion 24. The width of the secondary absorbent 68 may be narrowed beyond the crotch portion 24 but may thus compromise the containment of liquid flowing or seeping from the primary absorbent. More preferably, the width outside the crotch portion is wider than in the crotch portion, and is from about 5 inches (127 mm) to about 12 inches (306 mm), alternatively from about 5.5 inches (140 mm) to about 7.5 inches (191 mm). Preferably, the width is about 6.5 inches (165 mm).

Figure 4:
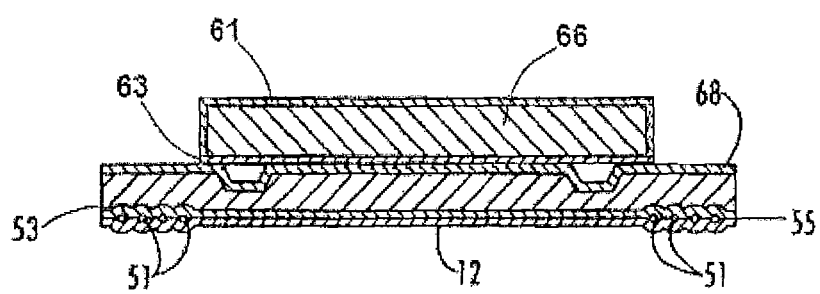
FIG. 4 is a cross section of the garment subassembly taken along line 4-4 of FIG. 2.

Referring to FIGS. 2, 3, and 4, the waist elastics 40, the body elastics 64, and the leg elastics 48, 50, 51 are generally covered by the front and back layer elements 19, 21 of the body side layer 14.

Both outer cover layer 12 and body side layer 14 are compliant and soft feeling to the wearer. The following description of materials from which the outer cover layer 12 can be made applies equally to the material of the body side layer 14.

The outer cover layer 12 may be liquid pervious, permitting liquids to readily penetrate into its thickness, or impervious, resistant to the penetration of liquids into its thickness. Outer cover layer 12 may be made from a wide range of materials, such as natural fibers (e.g. wood or cotton fibers), synthetic fibers (e.g. polyester or polypropylene fibers) or from a combination of natural and synthetic fibers or reticulated foams and apertured plastic films. The outer cover layer 12 may be woven, nonwoven such as spunbonded, carded, or the like. A suitable outer cover layer 12 is carded, and thermally bonded by means well known to those skilled in the fabric art. Alternatively, the outer cover layer 12 is derived from a spunbonded web. In preferred embodiments, the outer cover layer is spunbonded polypropylene nonwoven with a wireweave bond pattern having a grab tensile of 19 pounds as measured by ASTM D1682 and Do, a Taber 40 cycle abrasion rating of 3.0 as measured by ASTM Do and Handle-O-Meter MD value of 6.6 grams and CD value of 4.4 grams using TAPPI method To. Such spunbonded material is available from Kimberly-Clark Corporation, Roswell, Ga. The outer cover layer 12 has a weight of from about 0.3 ounce per square yard (osy) to about 2.0 osy, preferably about 0.7 osy.

The position and shape of the leg openings 44, 46 are important to avoid tightness in the crotch and groin area of the wearer, to obtain adequate buttocks coverage, and to prevent the panty 25 from tilting forward, e.g. tilting such that the front waist edge dips lower in relationship to the back waist edge. FIGS. 1 and 2 illustrate the most preferred design for leg fit and buttocks coverage. The shape of the curve across the top of the leg is important. If the curve is too deep, the panty 25 will shift downward and backward resulting in a short front waist, increased back length and bagginess in the seat of the panty. This would cause the panty 25 to appear tilted when worn as evidenced by an unevenness around the waist of the wearer.

Thus, the majority of the front leg edge portion 70 of the front portion of each leg opening 44, 46 is defined by a straight section 72 having a length "L2" at least about 70% of the length "L3" of the entire front leg edge portion 70. The straight section 72 should form an angle with the centerline A-A of between about 75 degrees and about 100 degrees, and most preferably about 90 degrees.

With the panty subassembly 10 laid out flat as in FIG. 1, the majority of the back leg edge portion 74 of the back portion of each leg is defined by a straight section 76 having a length "L4" at least about 70% of the length "L5" of the entire back leg edge portion 74. The straight section 76 forms an acute angle with the longitudinal centerline A-A of the subassembly 10. More preferably, the straight section 76 of the back leg edge portion 74 forms an acute angle α with the centerline A-A of the panty 25 of between about 50 degrees and 65 degrees and most preferably about 60 degrees.

The majority of the edge 78 of the crotch portion of each leg opening 44, 46 is defined by a straight section 80 having a length "L6." Preferably, the straight sections 80 are straight for at least about 70% of the entire lengths "L7" of the respective edges 78.

Each back leg edge portion 74 includes an arcuate section "A1" extending from one end 81 of the respective straight section 76 to a second end 82 connecting the respective back leg edge portion.

Each front leg edge portion 70 includes an arcuate section "A2" extending from one end 84 of the respective straight section 72 to a second end 86 connecting the respective front leg edge portion 70 to the front end of edge 78 of the respective crotch portion.

The shape of the arcuate section "A2" at the inner groin area is important. If the arc is too shallow, tightness may be experienced at the inner groin area.

The preferred narrow crotch width reduces coverage of the buttocks. To compensate for such reduction, the arcuate section "A1" is preferably adjusted toward back waist portion 22, such that the end 82 of the arcuate section "A1" should be positioned slightly forward of centerline B-B as shown in FIGS. 1 and 2.

The waist, leg, and body elastics 40, 48, 50, 64 respectively are attached to the panty subassembly 10, generally between the outer cover layer 12 and the body side layer 14, using apparatus and processes described hereinafter.

Materials suitable for elastics include a wide variety including but not limited to elastic strands, yarn rubber, flat rubber (e.g. as bands), elastic tape, film-type rubber, polyurethane, and, tape-like elastomer, or foam polyurethane or formed elastic scrim. Each elastic may be unitary, multipart, or composite in construction.

Waist elastic 40 is typically about 0.5 inch (13 mm) wide. The elastic may comprise threads, ribbons, a film, or composite. The threads or ribbons may be multiple and may be applied as a composite. Preferably, the waist elastic is threads, more preferably four threads are used as the elastic and the threads are spaced about 0.17 inch (4.3 mm) apart. The threads may be made of any suitable elastomeric material. One suitable material is spandex such as Lycra® threads available from Dupont located in Wilmington, Del. Suitable waist elastics include threads having a total decitex (g/1000 m) of about 3760 for 0.5 inch (13 mm) wide elastic. Adhesive 55 is used to bond the elastic between the outer cover layer 12 and the body side layer 14. A suitable adhesive includes, for example Findley H2096 hot melt adhesive, available from Findley Adhesives, Milwaukee, Wis.

The leg elastics 48, 50, and crotch elastic 51, including multiple threads in each, are typically about 0.5 inch (13 mm) wide. The elastic may comprise threads, ribbons, a film or composite. The threads, ribbons, etc., may be multiple and may be applied as a composite. The front leg elastics and the crotch elastics may be threads, preferably numbering three threads which are spaced about 0.17 inch (4.3 mm) apart. Back leg elastics numbering up to six threads may have a width of about 0.75 inch (19 mm) and a spacing of about 0.15 inch (3.8 mm) apart. The threads may be made of any suitable elastomeric material. One suitable material is spandex such as Lycra® threads available from Dupont, Wilmington, Del. Suitable leg elastics include threads having a total decitex (g/1000 m) of about 3760 for a 0.5 inch (13 mm) wide elastic. Adhesive 55 is used to bond the several elastics 48, 50, and 51 to the outer cover layer 12, the body side layer 14, and the support sheet 53.

To provide a snug leg fit and to draw up the sides of the crotch portion 24 to a cradle to receive the primary absorbent, the leg elastics 48, 50, and the crotch elastics 51, are elongated when applied to the layers 12 and 14 respectively. Preferably, the leg elastics 48, 50 are applied in multiple segments, with the amount of elongation of each segment while being incorporated into the subassembly 10 being determined according to the position to be occupied by the respective segment. In the case of only front and back leg elastics, the front leg elastics are elongated less than the back elastics. In the case of front elastics, back elastics, and crotch elastics, the front and crotch elastics are elongated less than the back elastics. Preferably, the front and crotch elastics are elongated to about 150% and the back elastics along the leg openings are elongated to about 250% The differing tensions allow easier attachment of the primary absorbent pad 66, less tightness in the groin area, and less bunching of the crotch portion 24 caused by high leg elastic retraction. The back leg elastic is under higher elongation to help keep the seat of the panty from creeping up with movement during use.

Figure 6:
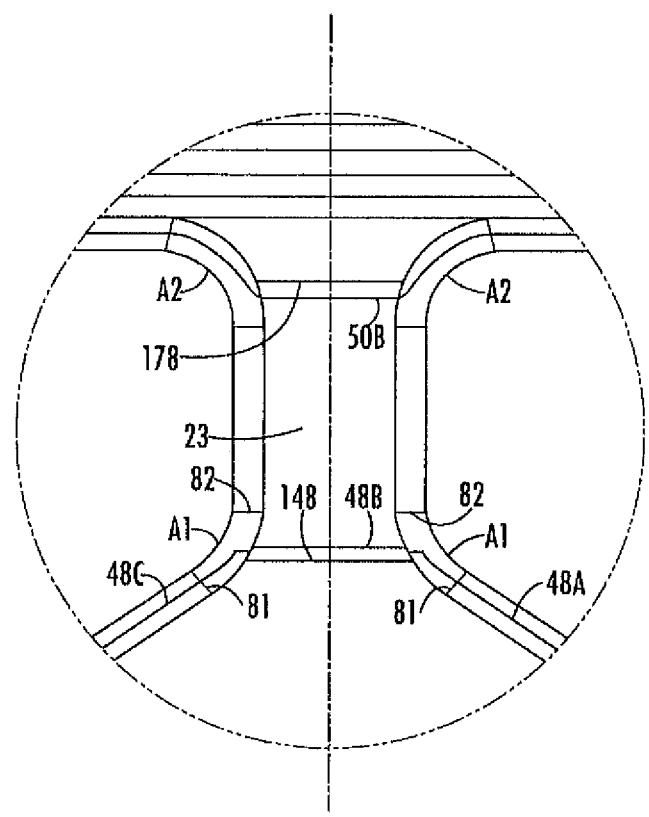
FIGS. 6 and 7 are enlarged cut-away views of a fragment of the subassembly of FIG. 1, particularly showing cross-crotch elastics in detail.
Figure 7:
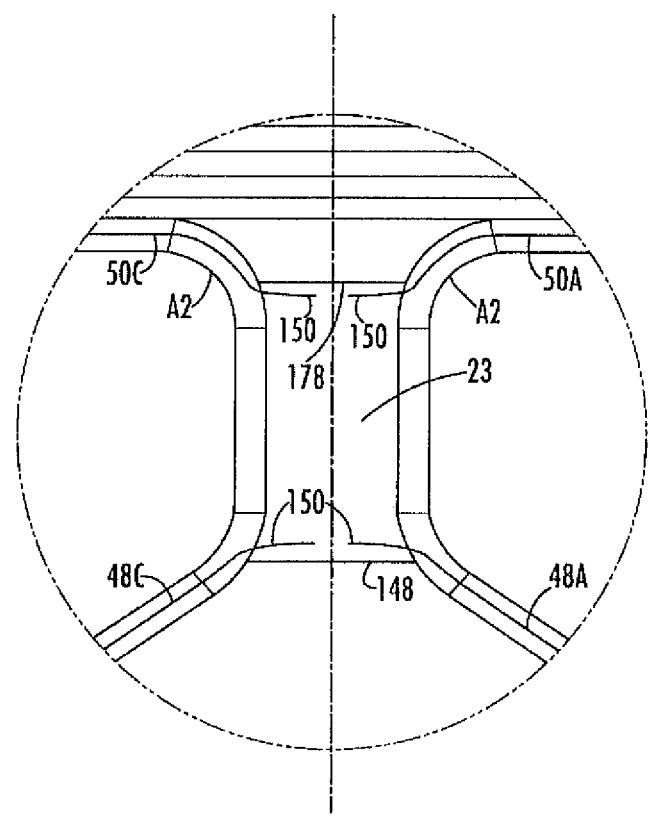

Referring now to FIGS. 1, 6, and 7, the suggested six (back) and three (front) threads of elastic on the respective back and front leg elastics 48 and 50 are each represented as single threads 112 of elastic. The following description of the characteristics and use of the single threads applies to the usual multiple threads suggested above.

The composite of the elastics extending about each of the leg openings 44 and 46 comprises a portion of the back leg elastics 48, a portion of the front leg elastics 50, and one of the left and right crotch elastics 51. Referring specifically to FIGS. 1, 6, and 7, the back leg elastic 48 extends, as a first section 48A, from a first locus 92 at or propinquant the edge 28 of the subassembly, width-wise across the subassembly at a substantially consistent acute angle .alpha. with the centerline A-A that takes it toward a first edge of the subassembly at front waist portion 18, and generally following the back leg edge portion 74 of the leg opening 46 along the straight section 76A and onto the first arcuate section "A1" toward the crotch portion 24, generally terminating in the first arcuate section "A1," at or near the crotch portion 24. Back leg elastic 48 extends, as a second section 48B, from the first arcuate section "A1" across the crotch portion to the second arcuate section "A1." From the second arcuate section "A1," the back leg elastic 48 extends, as a third section 48C, at an acute angle .alpha. with the centerline A-A away from the front waist portion 18, and generally following the back leg edge portion 74 of the leg opening 44 along the straight section 76B to a second locus 94 at or propinquant edge 34. In the flat configuration shown for the subassembly in FIGS. 1, 6, and 7, sections 48A and 48C are elongated 250%, while section 48B is relaxed, and under no substantial elongation. Preferably, section 48B includes a modest amount of slack in the elastic.

The front leg elastic 50 extends, as a first section 50A, from a third locus 96 at or propinquant the side edge 26 of the subassembly width-wise across the subassembly and generally following the front leg edge portion 70 along its longitudinal straight section 72A, and onto the first arcuate section "A2" toward the crotch portion 24, generally terminating in the first arcuate section "A2," at or near the crotch portion 24. Front leg elastic 50 extends, as a second section 50B, from the first arcuate section "A2" across the crotch portion to the second arcuate section "A2." From the second arcuate section "A2," the front leg elastic 50 extends, as a third section 50C, width-wise across the subassembly and generally following the front leg edge portion 70 along its longitudinal straight section 72B to a fourth locus 98 at or propinquant side edge 32. In the flat configuration shown for the subassembly in FIGS. 1, 6, and 7, sections 50A and 50C are elongated 150%, while section 50B is relaxed, and under no substantial elongation. Preferably, section 50B includes a modest amount of slack in the elastic.

Thus, in the embodiment seen in FIGS. 1, 2, 6, and 11, the front and rear leg elastics extend across the width W1 of the subassembly 10 as one or more continuous threads.

The crotch elastics 51 extend generally between the back and front leg elastics 48 and 50, with respective ends of the crotch elastics generally being disposed at or near the arcuate sections "A1" and "A2." Accordingly, the elastic properties extant about each leg opening result from the combined contributions of the respective back leg section (e.g. 48A), the respective front leg section (e.g. 50A), and the respective crotch elastic 51.

The reason for providing leg elastics in multiple sections is at least two-fold. First, using multiple sections of elastics facilitates placing of the elastics on the outer cover layer 12 while maintaining advantageous production speeds. As suggested in FIGS. 1, 8, and 9, the subassembly of e.g. FIG. 1 is made as a sequence of such subassemblies in a continuous web 100, with the width "W1" of the subassembly disposed in the "with machine" direction of the processing apparatus. In such arrangement, the front and back waist elastics 40, the front and back body elastics 64, and the front and back leg elastics 48, 50 can all be assembled into the subassembly by appropriate continuous feeding of respective continuous threads of elastics into the processing apparatus in the "with machine" direction while the web 100 continuously advances in the "with machine" direction at a constant speed.

Given the orientation of the crotch elastics at essentially 90 degrees to the direction of advance of the web 100, placing the crotch elastics as a portion of a continuous element of either the front or back leg elastics would suggest either (1) momentarily and regularly stopping the advance of the web 100 while the crotch elastic is fed into place, or (2) severely slowing the web 100 and severely driving an elastics guide, in a direction transverse to the web in order to apply the crotch elastic while the web was thus slowed. In either scenario, severe stresses would be placed on the respective drive apparatus, as well as on the web. The invention contemplates, rather, that the crotch elastics are placed in the subassembly 10 as a separate operation placing separate elastics segments, where the crotch elastics segments are first elongated and oriented transverse to the web 100, and are then placed on the web as the web passes the appropriate operating station (not shown) subsequent to placing the leg, body and waist elastics in the subassembly, though the sequence of placing the elastics is not critical.

Figure 8:
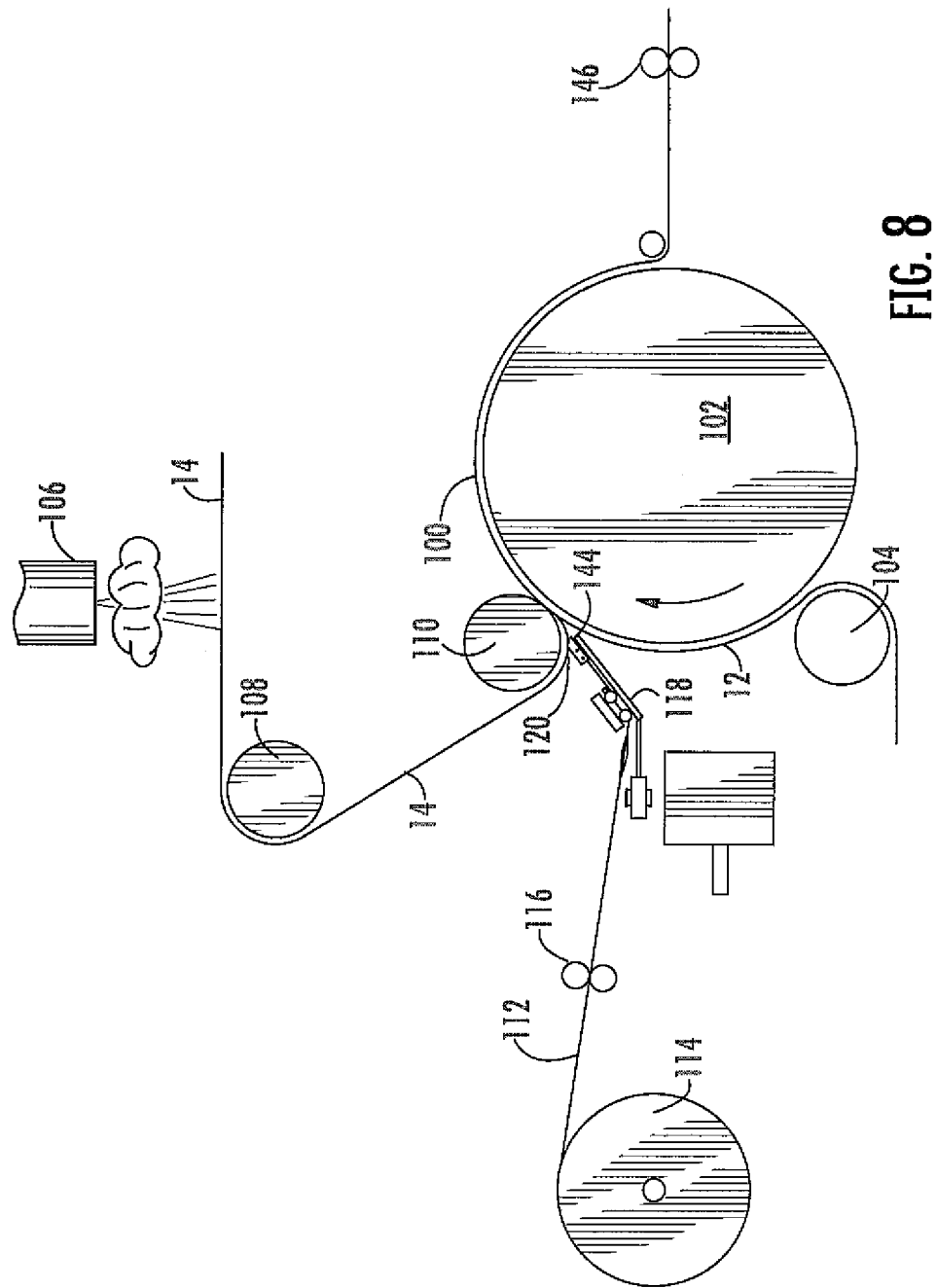
FIG. 8 is a side elevation view of an equipment layout for fabricating and processing subassemblies according to another aspect of the invention.
Figure 9:
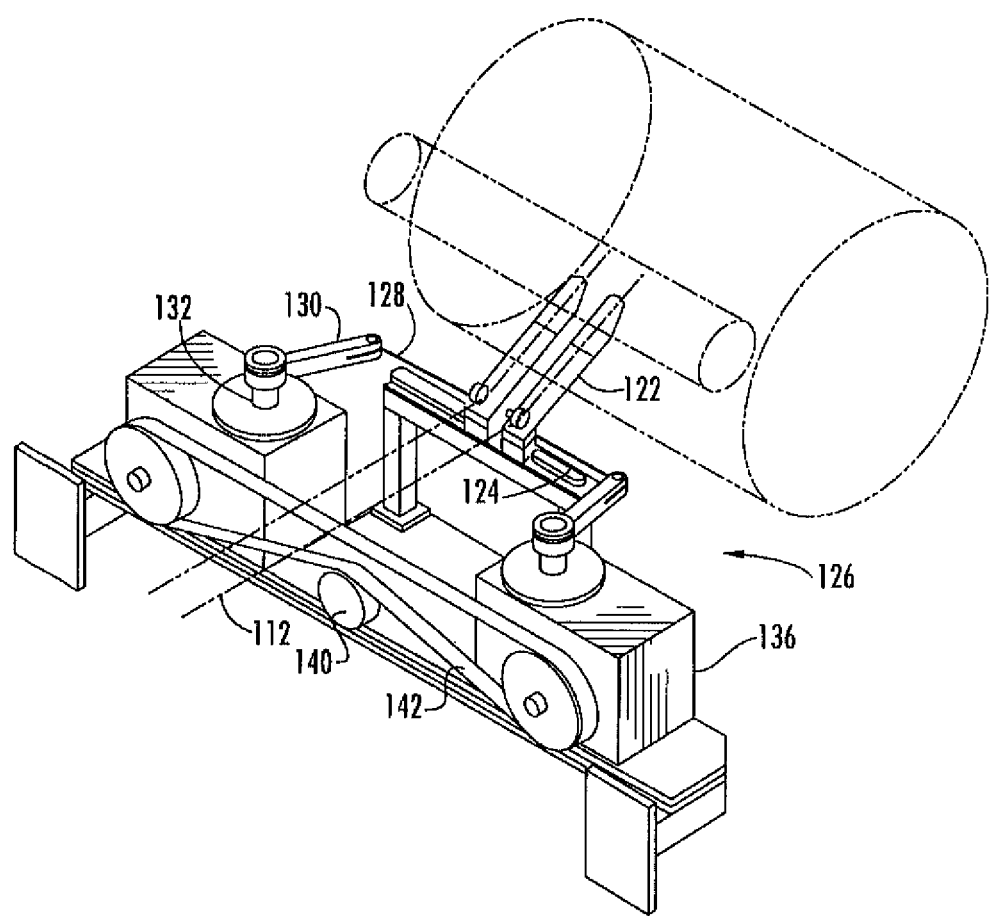
FIGS. 9 and 10 are pictorial views of a nip area of the elevation shown in FIG. 8.

Referring now to FIGS. 8 and 9, a first continuous web, which ultimately becomes cover layer 12, is pressed against the assembly roll 102 by turning roll 104. A second continuous web, which ultimately becomes body side layer 14, passes under adhesive applicator 106 and over turning rolls 108 and 110, and is pressed against the assembly roll 102 by turning roll 110. Elastic threads 112 are fed from a continuous supply 114 of elastic thread through feed nip 116, through thread guides 118 and sets of guide fingers 120A and 120B, and between cover layer 12 and body side layer 14 at the nip formed by assembly roll 102 and turning roll 110.

Figure 10:
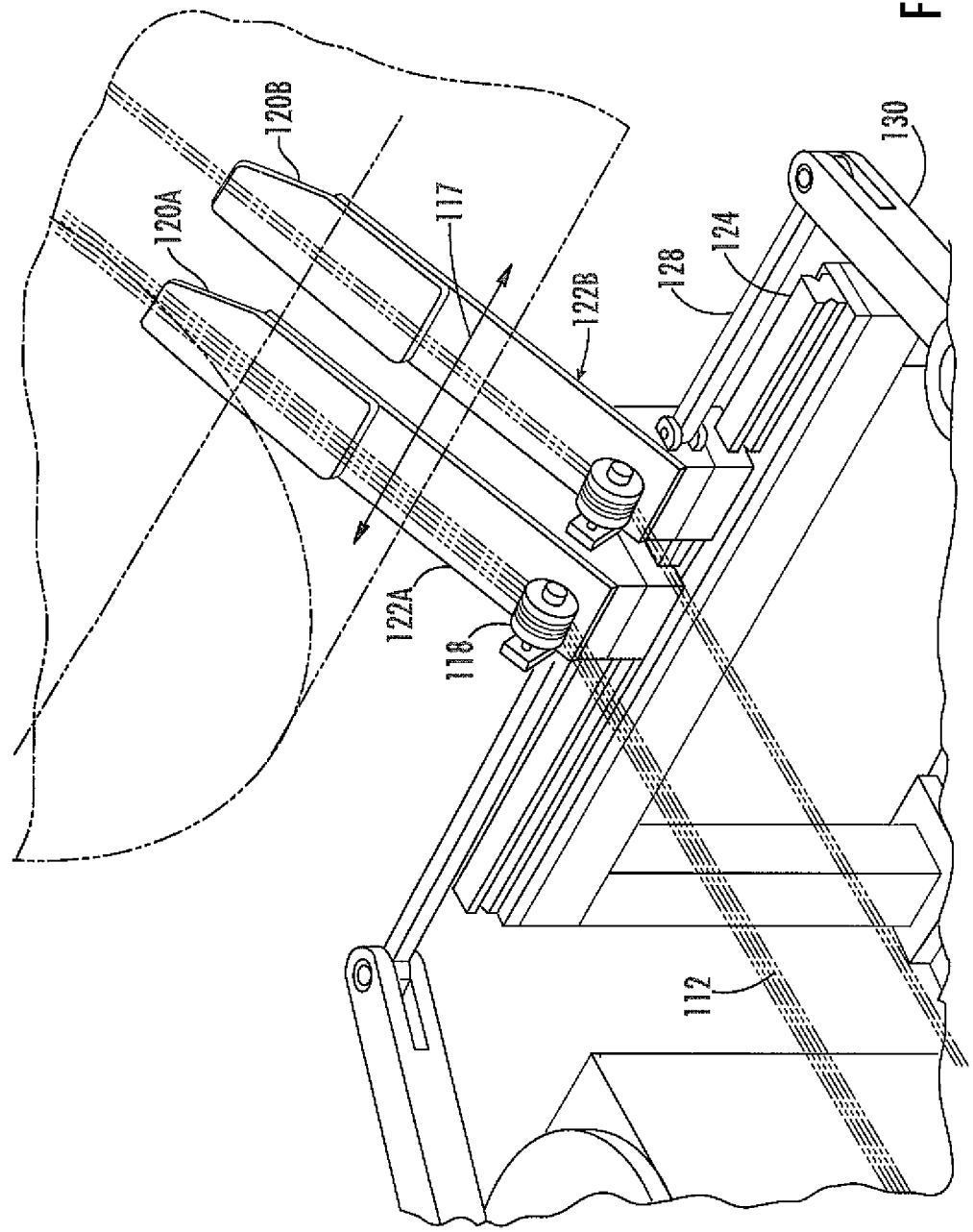
Figure 11:
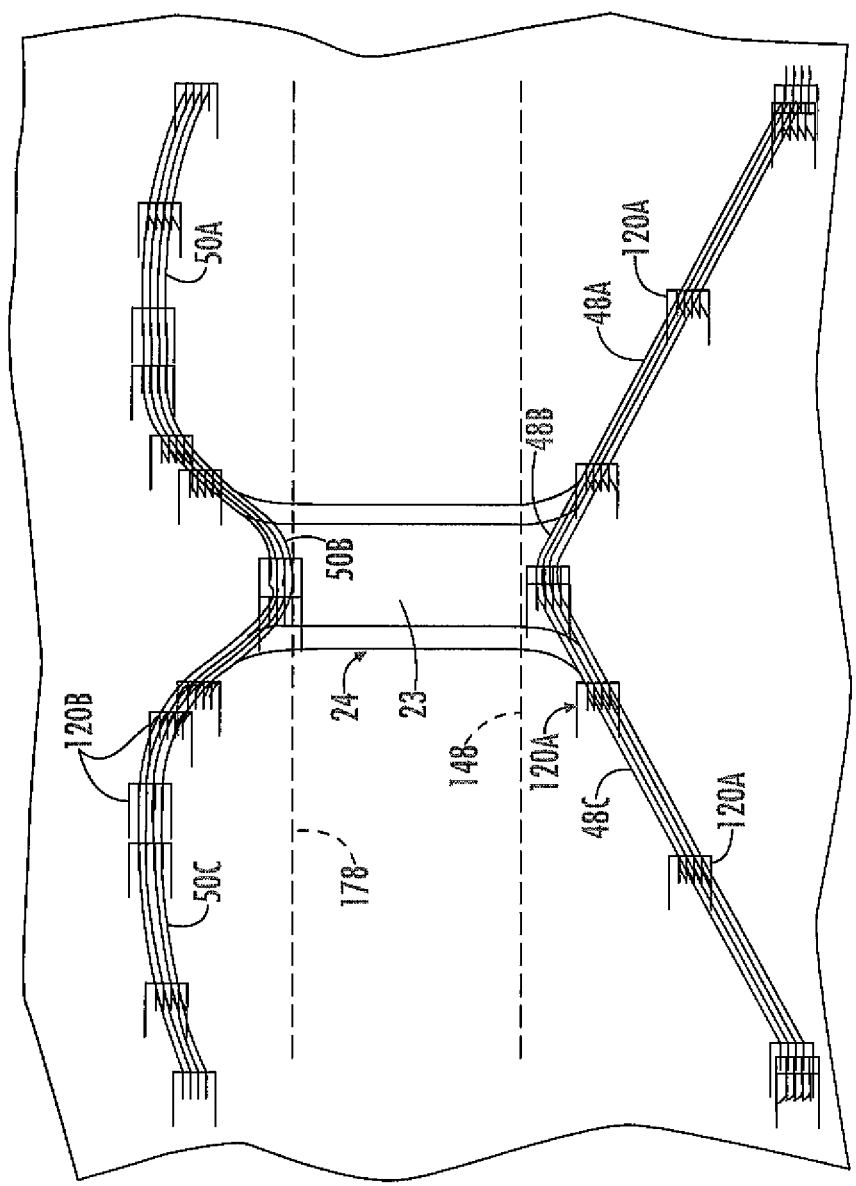
FIG. 11 is a plan view showing transverse positioning of front and back leg elastics along an advancing web as an outer cover layer and a body side layer are being joined according to an aspect of the invention.

Referring especially to FIGS. 10 and 11, thread guides 118 and corresponding sets of guide fingers 120A and 120B are elements of lateral guides 122A and 122B respectively. Each of the lateral guides 122A and 122B is mounted on a transverse slide bar 124 for sliding transverse to the with machine direction of travel of the webs. Each lateral guide 122 is connected to a transverse drive mechanism 126 including linkage arms 128 and 130, vertical drive shaft 132, and a cam follower. The cam followers follow the corresponding cams inside the respective cam housings. The cams are linked to the machine drive shaft 140 by drive belt 142. Thus, the cams, and correspondingly the thread guides and the sets of guide fingers, move transversely with respect to the with machine direction of the webs as the drive shaft turns. The end result is that rotation of the processing line drive shaft 140 effects transverse motion of the thread guides and the sets of guide fingers, as indicated by the arrows in FIG. 10, in cooperation with the design of the cams and cam followers.

Referring to FIG. 8, the guide fingers 120 are positioned close to the nip 144 so that they closely control the transverse positions of the elastics with respect to the webs 12 and 14 as the webs 12 and 14 enter the nip 144 and correspondingly trap the elastics between them, fixing the position of the elastics between them by means of adhesive 55. Accordingly, the guide fingers 120 are preferably physically positioned, and provide guidance to the threads of elastic, within one inch of the nip 144. To the extent the fingers can be placed closer to the nip 144, they provide more positive guidance to the elastic. By careful design of the guide fingers 120, and by careful control of the positioning of the guide fingers 120 with respect to nip 144, the guide fingers 120 can be advantageously positioned within 0.5 inch of the line of contact defined at the nip between roll 102 and 108.

The limitation on how close the guide fingers 120 can be placed to the nip is controlled by the ability to design fingers which can affirmatively guide the threads of elastic while avoiding having the fingers themselves drawn into the nip. The criticality of urging the fingers as ultimately close as possible to the nip can be attenuated by directing the threads 112 onto the adhesive-coated layer 14 ahead of nip 144, preferably instantaneously ahead of the nip 144, as suggested by the depiction in FIG. 8. By directing the threads of elastic onto layer 14 ahead of the nip, the open distance spanned by the threads between the fingers 120 and the adhesive-coated layer 14 is minimized, being held to less than 0.5 inch, for example 0.25-0.375 inch (6 mm to 10 mm).

The transverse movement of the lateral guides 122, and thus fingers 120, as the webs advance along the processing line, creates transverse positioning of the elastics threads 112 with respect to the with machine direction of the advancing webs 12 and 14. FIG. 11 shows the pattern of transverse movement of the sets of guide fingers 120A and 120B relative to the movement of the web in the with machine direction, along the processing line. In FIG. 11, the sets of fingers 120A and 120B are depicted at several locations along the front and back edges of the leg openings 44, 46, to indicate that it is the positioning of the sets of fingers 120A and 120B, and the dynamic changing of that positioning by the drive mechanism 126, that determines the instantaneous transverse location of the elastics in the web at any point and time while the elastics are being placed in the web at nip 144 as shown in FIGS. 8-11. Comparing FIGS. 1, 10, and 11, it is seen that the set of fingers 120A generally places the threads of the back leg elastics generally parallel to each other in the web, while the set of fingers 120B generally places the threads of the front leg elastics generally parallel to each other in the web, both along their respective portions of the designed paths defining the front leg edge portion 70 and back leg edge portion 74 of the leg openings 44 and 46. The threads of elastic deviate slightly from their parallel relationships with each other as the elastic threads traverse paths that deviate from the with machine direction, the distance between the threads 90 being generally constant as they emerge from the fingers 120. Such deviations from the parallel, resulting from the cross machine traverse of the elastics, are included herein within the phrase "generally parallel" as respects the relationships of the threads of elastic to each other.

It will be understood that FIG. 11 represents only one panty in the continuous sequence of panty subassemblies 10 contained in the web 100 passing through nip 144. It will also be understood that the web passing through the nip 144 is further acted upon at cutter 146 to cut away material from the web 100 in creating the leg openings 44 and 46.

In general, then, webs 12 and 14 are provided as substantially endless rolls from unwind stands (not shown). Web 14 is typically provided as front and back layer elements 19 and 21. Space 23 separates the elements 19 and 21, and generally corresponds with the crotch portion and the portion of the web 12 which is cut out to form leg openings 44 and 46. Adhesive 55 is applied to the front and back elements 19 and 21 of web 14 by adhesive applicator 106. Webs 12 and 14 are joined adhesively, with elastic threads being interposed between webs 12 and 14 at nip 144, and with space 23 interposed between the front and back elements 19, 21 of the body side layer 14. The transverse positions of the elastics change according to a pre-set path of transverse movements, driven by the drive shaft 140 which drives and times the several operations along the processing line. The threads of elastic 112, as placed by the guide fingers 120, traverse respective paths that ultimately follow the front and back edges of the leg openings 44 and 46, as defined at cutter 146, in registration with the advance of the web, and accordingly, with the advance of the series of panty subassemblies 10 being defined in the web at nip 144 and cutter 146. The portions of the threads of elastic located along the front and back edges of the leg openings are stretched. The portions traversing the crotch portion are relaxed. The crotch portions of the elastic are separately placed in the subassembly 10 at a later processing station, preferably downstream from the cutter 146.

Figure 12:
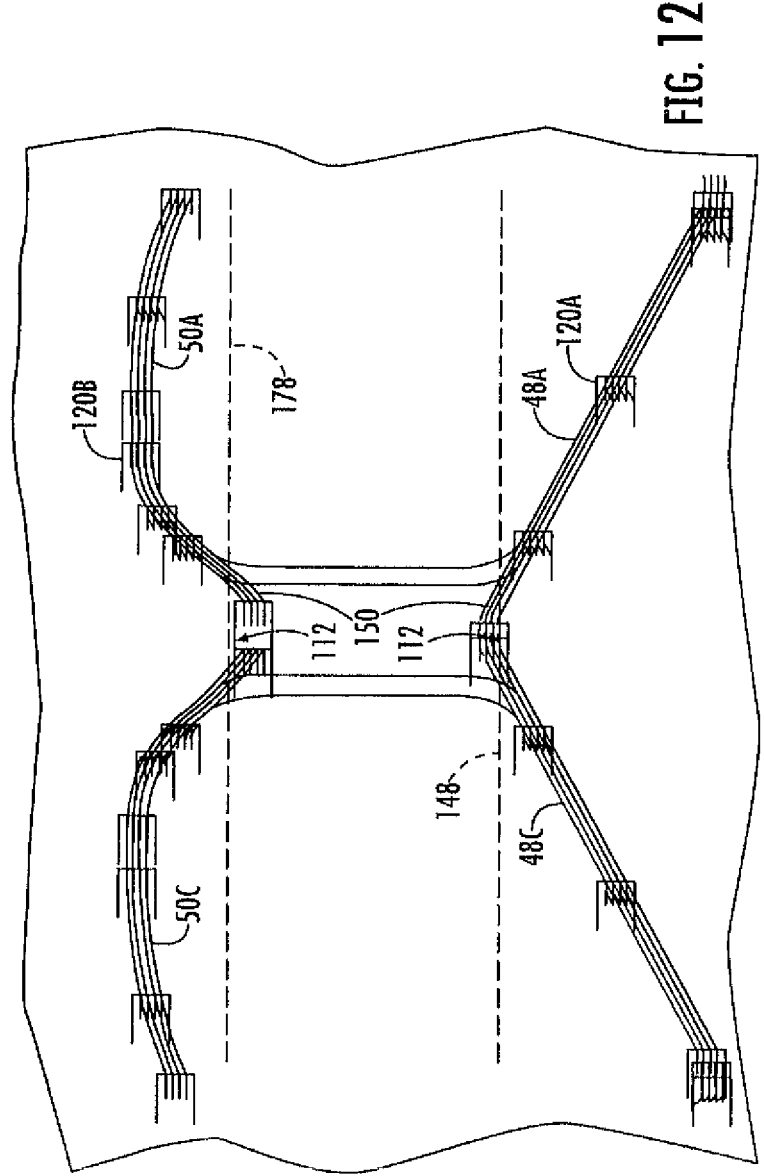
FIG. 12 is a plan view as in FIG. 10, showing an alternate pattern for elastic threads.

A second embodiment of the subassembly is illustrated in FIG. 12. In the second embodiment, the front edge 148 of back layer element 21 is disposed rearwardly of that same edge 148 as depicted in the embodiment of FIG. 10, while the guide fingers 120A traverse the same path as in FIG. 10. Accordingly, as the threads of elastic 112 extend across the crotch portion 24, the threads 112 are guided forwardly of edge 148, into space 23, and are thus not held between the layers 12 and 14, and thus are not controlled by the adhesive on layer 14. Rather, the tension is maintained on the threads of elastic 112 across the crotch portion 24, such that the threads retract along the edge 148 of the layer element 21 in a configuration that loosely resembles a rope under tension. The rope is subsequently cut such that the cut portions of the threads retract to positions generally defined by the intersection of the edge 148 of the back layer element 21 and the path of the threads adhesively held between layer 12 and the back layer element 21. Thus, the threads 112 generally include loose intermediate ends 150 after being cut, as shown in FIG. 7.

Body elastics 64 and waist elastics 40 can be incorporated at nip 144 in the conventional manner of providing stationary feeds and guides at the nip.

Figure 13:
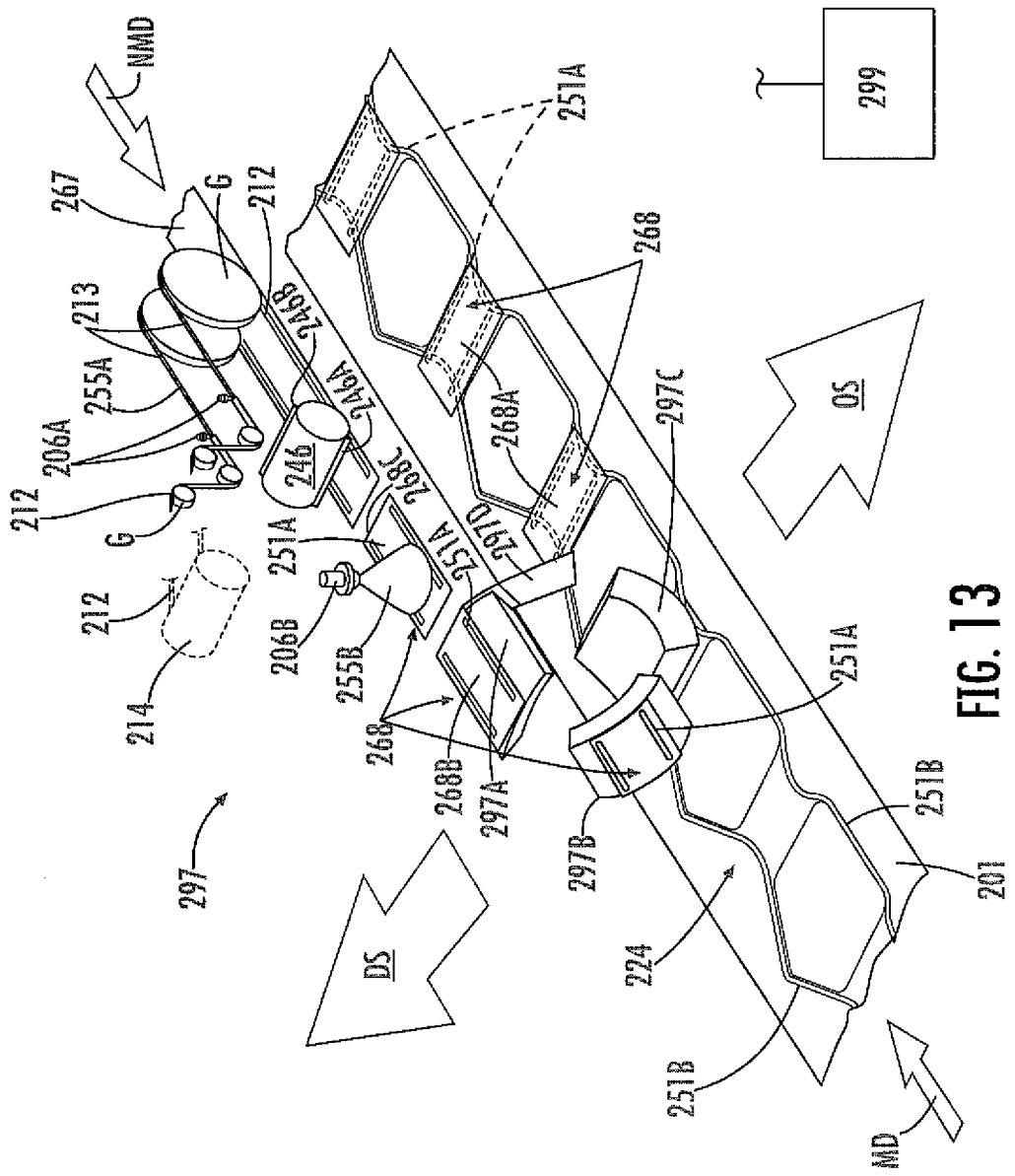
FIG. 13 is a perspective view showing steps in a method for cutting a plurality of elastics and attaching the elastics to a secondary absorbent according to another aspect of the invention.

In another embodiment of the invention shown in FIG. 13, a section of web processing equipment 297 is shown including a drive side DS and an operator side OS. As generally shown, a plurality of elastic threads 212 are attached to a stain shield or secondary absorbent web 267, and the secondary absorbent 267 and attached elastic threads 212 are cut to create a plurality of stain shields 268 having respective elastic pieces or sections 251A attached thereto. The elasticized stain shields 268 are maneuvered as shown and attached to a garment web 201 to form a garment blank subassembly. This garment blank subassembly is similar in many ways to the embodiments described above; therefore, only certain features of this embodiment are described below for the sake of brevity and reference is made to the foregoing descriptions for like or similar components of the garment blank subassembly to enable this aspect of the invention.

With more particular reference to FIG. 13, the processing equipment 297 supplies the plurality of elastic threads 212 from an elastic thread roll 214 generally in a machine direction MD. The elastic threads 212 are routed by a series of guide rollers G in a known manner and are attached in a stretched condition in a non-machine direction (NMD) in this example to the secondary absorbent web 267 using an adhesive 255A. As shown, the adhesive 255A is applied intermittently to the elastic threads 212 by a plurality of applicators 206A to form a plurality of adhesive gaps 213 along the elastic threads 212. The cutter 246 cuts the secondary absorbent web 267 into the stain shields 268 at each adhesive gap 213. As further shown, the stain shield 268 the resultant sections 251A are attached to a first or inner side 268B, which opposes a second or outer side 268A discussed further below.

The exemplary cutter 246 shown in FIG. 13 is a roller cutter having a plurality of blades 246A,B attached thereto for cutting the elastic sections 251A at the adhesive gaps 213 as discussed above. The cutter 246 is controlled by a controller 299 disposed on the operator side OS of the processing equipment 297 in this example. Those skilled in the art will instantly recognize that the controller 299 can be a computer or a programmable logic controller, which can be programmed to cut the elastic threads 212 at the adhesive gaps 213 based on a passage of time or a sensed length of passing elastic threads 212 to create the sections 251A. As shown, each end of each section 251A, which formed the gaps 213 in the elastic threads 212 before the elastic threads 212 were cut, retract after being cut to create a retraction area 268C on the outer side 268B. In this example, the sections 251A are from about one (1) inch to about three (3) inches in length.

As further shown in FIG. 13, a second adhesive applicator 206B applies a second amount of adhesive 255B to the outer sides 268B of the stain shields 268. As shown, a plurality of applicator assembly segments 297A-D subsequently maneuver or rotate the adhesive coated stain shields 268 transverse to the machine direction MD. As further shown, the applicator assembly segments 297A-D affix the adhesive coated outer sides 268B and the underlying elastic sections 251A to the garment web 201 with the inner sides 268A facing upward or outward from within a crotch area or portion 224. As shown, the inner sides 268A are located between a plurality of garment elastics 251B. In this manner, the individual elastic sections 251A are rapidly manipulated, positioned and attached to the crotch area 224 without having to maneuver the entire garment web 201 and/or cut the elastic threads 212 and apply the elastic sections 251A to the crotch portions 224 through acute angles at high machine speeds.

Wherever herein this teaching refers to "multiple" elements, e.g. multiple threads of elastic or multiple paths of traverse, any two or more such elements are included.

Having thus described the invention in full detail, it will be readily apparent that various changes and modifications may be made without departing from the spirit of the invention. All such changes and modifications are contemplated as being within the scope of the present invention, as defined by the following claims.

That which is claimed is:

1. A disposable garment comprising:
   a front body portion, a back body portion, and a crotch portion in between the front body portion and the back body portion, the front body portion and the back body portion being connected together to form a waist opening, a first leg opening, and a second leg opening, the first leg opening being surrounded by a first front leg edge portion, a first back leg edge portion, and a first crotch leg edge portion positioned in between the first front leg edge portion and the first back leg edge portion, the second leg opening being surrounded by a second front leg edge portion, a second back leg edge portion, and second crotch leg edge portion positioned in between the second front leg edge portion and the second back leg edge portion;
   an absorbent located at least within the crotch portion;
   a first elastic having a first end near a first side edge of the front body portion and extending along the first front leg edge portion and the second front leg edge portion to a second end near a second side edge of the front body portion, the first elastic having been cut to form a first front intermediate end spaced from a second front intermediate end;
   a second elastic having a first end near a first side edge of the back body portion and extending along the first back leg edge portion and along the second back leg edge portion to a second end near a second side edge of the back body portion, the second elastic having been cut to form a first back intermediate end spaced from a second back intermediate end; and
   a plurality of opposing crotch elastics extendably affixed to opposing edges of the crotch portion in between the first elastic and the second elastic on each side of the crotch portion.

2. A disposable garment as in claim 1, wherein the intermediate ends are retracted.

3. A disposable garment as in claim 2, wherein the retracted intermediate ends are free from adhesive.

4. A disposable garment as in claim 1, wherein the first and second elastics have been cut into a plurality of elastic sections.

5. A disposable garment as in claim 1, wherein the waist opening is surrounded at least in part by a waist elastic.

6. A disposable garment as in claim 5, wherein the waist elastic comprises threads, ribbons, a film, or a composite.

7. A disposable garment as in claim 1, wherein the front body portion and the back body portion include body elastics positioned between the waist opening and the leg openings.

8. A disposable garment as in claim 1, wherein the garment defines a length direction and a width direction transverse to the length direction, wherein the crotch elastics extendably affixed to opposing edges of the crotch portion extend in the length direction of the garment.

9. A disposable garment as in claim 1, wherein the garment defines a length direction and a width direction transverse to the length direction, wherein the crotch portion is free from continuous elastics spanning the width direction of the garment.

10. A disposable garment as in claim 1, wherein the opposing crotch elastics and the first and second elastics overlap.

11. A disposable garment as in claim 1, wherein the garment has a body side liner positioned to face the wearer.

12. A disposable garment as in claim 11, wherein the body side liner comprises a front body portion element and a back body portion element which are separate from one another.

13. A disposable garment as in claim 1, wherein the intermediate ends are adjacent the crotch portion.

14. A disposable garment as in claim 1, wherein the intermediate ends extend over the crotch portion.

15. A disposable garment as in claim 1, wherein at least one of the first or second elastic is angled with respect to a longitudinal centerline of the disposable garment.

16. A disposable garment comprising:
   a front body portion, a back body portion, and a crotch portion in between the front body portion and the back body portion, the front body portion and the back body portion being connected together to form a waist opening, a first leg opening, and second leg opening, the first leg opening being surrounded by a first front leg edge portion, a first back leg edge portion, and a first crotch leg edge portion positioned in between the first front leg edge portion and the first back leg edge portion, the second leg opening being surrounded by a second front leg edge portion, a second back leg edge portion, and second crotch leg edge portion positioned in between the second front leg edge portion and the second back leg edge portion;
   an absorbent located at least within the crotch portion;
   a first elastic having a first end near a first edge of the front body portion and extending along the first front leg edge portion and the second front leg edge portion to a second end near a second edge of the front body portion, the first elastic having been cut to form a first front intermediate end spaced from a second front intermediate end;
   a second elastic having a first end near a first edge of the back body portion and extending along the first back leg edge portion and along the second back leg edge portion to a second end near a second edge of the back body portion, the second elastic having been cut to form a first back intermediate end spaced from a second back intermediate end;
   a plurality of opposing crotch elastics extendably affixed to opposing edges of the crotch portion in between the first elastic and the second elastic on each side of the crotch portion;

a body side liner positioned to face the wearer, wherein the body side liner comprises a front body portion element and a back body portion element which are separate from one another; and wherein the crotch portion defines a width and is free from continuous elastics spanning the width.

* * * * *